United States Patent [19]
Kohr

[11] Patent Number: 5,223,435
[45] Date of Patent: Jun. 29, 1993

[54] AMINO ACID SEQUENCE DETERMINATION WITH MOBILE PEPTIDE

[75] Inventor: William J. Kohr, San Mateo, Calif.

[73] Assignee: Genetech, Inc., South San Francisco, Calif.

[21] Appl. No.: 782,714

[22] Filed: Oct. 25, 1991

Related U.S. Application Data

[63] Continuation-in-part of Ser. No. 577,404, Sep. 4, 1990, abandoned, which is a continuation of Ser. No. 871,736, Jun. 6, 1986, abandoned.

[51] Int. Cl.$^5$ .............................................. G01N 33/00
[52] U.S. Cl. ...................................... 436/89; 422/68.1; 422/70; 422/116; 530/408; 530/412; 530/417; 530/810; 530/817; 935/88; 210/198.2; 210/659
[58] Field of Search ...................... 436/89; 422/69, 70, 422/81, 102, 116, 68.1; 210/198.2, 635, 656, 659, 657; 530/408, 412, 417, 810, 817; 935/88

[56] References Cited

U.S. PATENT DOCUMENTS

| | | | |
|---|---|---|---|
| 2,525,497 | 10/1950 | Monfried | 210/290 |
| 3,615,235 | 10/1971 | Hrdina | 436/89 X |
| 3,787,317 | 1/1974 | Jaworek | 210/502.1 X |
| 4,065,412 | 12/1977 | Dreyer | 422/129 X |
| 4,267,056 | 5/1981 | McClure | 422/70 X |
| 4,301,139 | 11/1981 | Feingers et al. | 210/198.2 X |
| 4,483,964 | 11/1984 | Urdea et al. | 422/121 X |
| 4,519,905 | 5/1985 | Stevens et al. | 210/198.2 |
| 4,548,904 | 10/1985 | Kent et al. | 436/89 |
| 4,665,037 | 5/1987 | Stolowitz | 436/89 |

Primary Examiner—James C. Housel
Assistant Examiner—Maureen M. Wallenhorst

[57] ABSTRACT

Sequential degradation of peptides for sequencing purposes by successive cleavage of amino acids from one end of the peptide chain is performed in an adsorption column with flows of the degradation reagents and wash liquids passing through the column in both directions. Migration of the peptide in one direction is thereby compensated by a subsequent migration in the other, and loss of peptide from the column over repeated cleavages is avoided. In preferred embodiments, the column contains two serially arranged adsorbent zones with differing adsorption characteristics, and the directions of flow of the various system components through the column are selected with a view toward a difference in peptide partitioning between the stationary and mobile phases in one zone vs. the other. The result is that any migration of the peptide occurring at any stage of a given cycle of the procedure occurs at a greater rate toward the zone interface than away from it. The overall effect after repeated cycles is a focusing of the peptide toward the center of the column without the need for covalent bonding of the peptide to a solid support.

19 Claims, 3 Drawing Sheets

AMINO ACID SEQUENCE DETERMINATION WITH MOBILE PEPTIDE

CROSS REFERENCE TO RELATED APPLICATIONS

This is a continuation-in-part of co-pending application Ser. No. 07/577,404, filed Sep. 4, 1990, now abandoned, which is a continuation of co-pending application Ser. No. 06/871,736, filed Jun. 6, 1986 now abandoned.

This invention relates to methods for the determination of the amino acid sequence of polypeptides and proteins, and equipment for making such determinations.

BACKGROUND OF THE INVENTION

The most widely used method of protein sequence analysis is the Edman degradation for the sequential removal of amino acid residues. In this scheme, amino acids are removed from the N-terminal end of the peptide in a two-step chemical process. The procedure for one cleavage is illustrated below.

disclosed by Datta, S., et al., *Biochem. and Biophys. Res. Commun.* 72:1296-1303 (1976) and Laursen, R. A., *J. Am. Chem. Soc.* 88: 5344-5346 (1966). The function of the coupling reaction is to make the peptide bond between the first and second residues more easily acid hydrolyzed than any of the other peptide bonds in the peptide.

After removal of excess coupling reagent and buffer, a cleavage reagent, anhydrous acid, is added to hydrolyze the activated peptide bond. The cleavage amino acid derivative can then be extracted with a suitable organic solvent. The residual peptide in which what was originally the second amino acid is now the N-terminal amino acid is left behind for subsequent cycles. The extracted derivative contains information regarding the identity of the initial N-terminal amino acid since the latter is incorporated in its structure. By differentiating among the twenty or so derivatives which can thus be formed on the basis of their side chain ($R_1$), the derivative formed after each cleavage can be identified and the amino acid ascertained. In the ideal situation, repetition of this process would result in identification of each residue of the peptide. However, it is not practi-

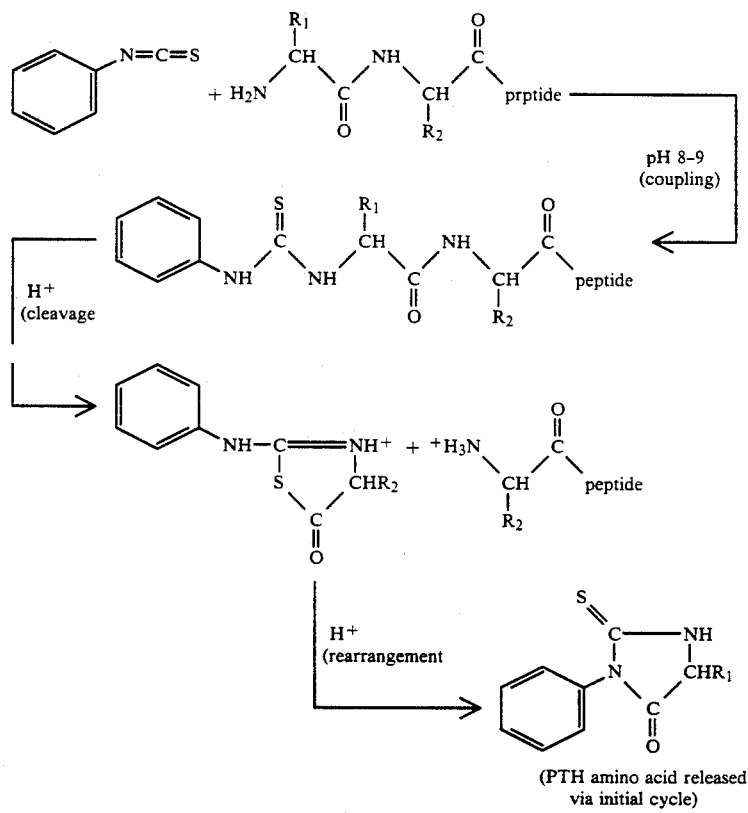

(PTH amino acid released via initial cycle)

The following is a description of this reaction scheme. All literature cited in this description is hereby incorporated herein by reference.

In the first step an activating group, termed a coupling reagent and illustrated above by phenylisothiocyanate (PITC), is attached to the free amino group of the N-terminal amino acid of the peptide whose sequence is to be determined. This reaction is performed in a buffer containing a coupling base at high pH (pH 8-9). While PITC is the most commonly used coupling reagent, other useful coupling reagents are methylisothiocyanate and pentafluorophenylisothiocyanate, as cal to carry out repetitive chemical reactions indefinitely, since the coupling and cleavage reactions never attain 100% yield. Although the coupled N-terminal peptide bond is more susceptible to acid hydrolysis than any other bond, random cleavage can and does occur.

The Edman process has been used in manual methods and in automated methods for amino acid sequence determination.

The manual procedures are most frequently used for sequence determinations of small peptides on short sections of proteins or when the cost of an automated sequencer cannot be justified. Many such methods have been reported; see Edman, P., *Protein Sequence Determinations*, S. B. Needleman, ed., Springer-Verlage, New York (1975), page 237, and Tarr, G. E., *Anal. Biochem.* 63:361-370 (1975). Most approaches first apply the protein or peptide to a support such as a paper strip. After the sample is dried, PITC in a solvent-buffer system such as dioxane or pyridine is contacted with the immobilized peptide. The coupling reaction may take several hours at 40°-50° C. for completion. It is important at this step that oxygen be excluded to prevent side reactions which block the N-terminal amino acid. After coupling is complete, the excess reagent and by-product (diphenylthiourea) are removed without loss of the coupling product, which is the phenylthiocarbamyl peptide (PTC-peptide). Several solvent systems have been suggested for this step, notably benzene and alcohol-ether, as disclosed in Fraenkel-Conrat, H., *J. Am. Chem. Soc.* 76:3606 (1954). Extraction with benzene alone to remove these byproducts is slow but effective in separating the excess reagent and byproduct from the coupled peptides. Faster extraction of reagent and by-product is achieved with ethyl acetate or an alcohol-ether mixture, but these will also extract small hydrophobic peptides.

After the first wash the PTC-peptide is cleaved into the anilinothiazolinone amino acid (ATZ-amino acid) and free peptide. Since internal peptide bond cleavage can occur under aqueous conditions as disclosed by Edman, P., et al., *Eur. J. Biochem.* 1:80-91 (1967), most procedures call for anhydrous acid, such as trifluoroacetic (TFA) or heptafluorobutyric acid (HFBA). This step is performed at a lower temperature than the coupling step, and water is excluded from the sample chamber. The cleavage of coupled residues is more difficult with prolyl or glycyl residues, and these may require a higher temperature or a longer reaction period. Overly vigorous hydrolysis conditions at this point can lead to spurious cleavage of internal peptide bonds.

In the final step, the ATZ-amino acid is extracted with benzene and ethyl acetate. The phase transfer is quantitative for most amino acid derivatives except ATZ-Arg and ATZ-His. Ethyl acetate alone will give better extraction of ATZ-Arg and ATZ-His but may also extract small hydrophobic peptides. Acetone is a satisfactory compromise if all traces of water and the acid cleavage reagent are removed earlier by drying under vacuum. The extracted ATZ-amino acid is unstable and must be converted to the stable PTH (3-phenyl-2-thiohydantoin) form by aqueous hydrolysis. The conversion is achieved by hydrolysis of the ATZ-amino acid to the phenylthiocarbamoyl amino acid (PTC-amino acid) intermediate followed by rearrangement to the PTH form. The benzene/ethyl acetate extract is evaporated to dryness under a stream of nitrogen and then dissolved in dilute HCl. The temperature is quickly brought to 80° C. and maintained for 10 minutes, then lowered. The solution is dried and dissolved in a small volume of buffer, whereafter the PTH-amino acid derivative is analyzed.

In general, amino acid sequence determinations are made by automated methods in equipment dedicated to that purpose. The chemistry employed in such automated methods is basically the same as that used in the manual procedure. Present automatic sequencers are based on either liquid phase (spinning cup) or gas phase methods. In the liquid phase instruments, the protein sample is spread out as a thin film on the inner wall of a rotating reaction cup. The protein is immobilized while liquid Edman reagents which are introduced into the reaction cup at the bottom move up over the protein film by centrifugal force. Liquids are removed from the top of the cup by means of a scoop protruding into a groove around the top of the cup.

A description of a spinning cup sequencer is given in the original paper by Edman, P., et al., *Eur. J. Biochem.* 1:80-91 (1967). In the operation of such sequencers, a solution of the sample is introduced into the cup and dried under vacuum while the cup is turning, thus forming a thin film on the lower walls of the cup. Sample size is generally around 100 to 300 nanomoles of sample dissolved in about 500 microliters of the appropriate solvent. After the sample has been dried the automatic cycle is started.

Coupling reagent (5% PITC in heptane) and buffer are then introduced into the spinning reaction cup. The buffer generally contains N,N-dimethyl-N-allylamine (DMAA) to maintain the alkaline pH needed for the coupling reaction. A suitable buffer containing DMAA and a detergent is sold under the trademark Quadrol. The coupling mixture spreads out over the protein film and dissolves it. The ensuing reaction proceeds for about 20 minutes at 55° C. After partial removal of PITC and solvent by vacuum, the coupling reaction is stopped by the introduction of benzene. The benzene precipitates the protein and carries off the excess PITC reagent and some of the breakdown products of PITC. If Quadrol is used as the buffer, the cup is washed with ethyl acetate to remove excess buffer and more of the breakdown products. After vacuum drying the protein remains in the cup as a white film.

Anhydrous heptafluorobutyric acid (HFBA) is then added to initiate cleavage. The volatile HFBA covers and dissolves the protein film and after only two to three minutes the N-terminal amino acid is cleaved as the ATZ-amino acid. Finally, the remaining HFBA is removed by vacuum, then the released ATZ-amino acid is extracted with butyl chloride and delivered to a fraction collector. A new residue is released to the fraction collector with each cycle of the above procedure.

The collected fractions of ATZ-amino acids now represent the sequential order of amino acid residues comprising the peptide or protein sample. The fractions can be converted to the more stable PTH-amino acid products. The solution is heated for 10 minutes in 1.0M HCl at 80° C. or 25% TFA in $H_2O$ at 60° C. After removal from the heat, all PTH-amino acid derivatives except PTH-Arg and PTH-His can be extracted with ethyl acetate. Liquid chromatography analysis at this stage is advantageous since there is no need to separate the two phases: all PTH-amino acids present can be determined in a single injection. For preconcentration purposes, the fraction is usually taken to dryness at low temperature prior to the chromatography.

The spinning cup sequencer suffers from the disadvantages of requiring the delivery of precisely calibrated reagent quantities. Otherwise, protein is easily washed from the cup and must be continuously cycled through successive precipitations and resolubilizations. This leads to protein loss and denaturation, and extenders such as Polybrene or blocked proteins are often required to aid in the precipitation of the test sample. The disadvantage of using protein extenders is that they are frequently hydrolyzed during cycles of Edman degradation. These hydrolyzed extenders contain free amino termini that are sequenced along with the test sample, thereby introducing interfering residues into the determination.

Automatic solid-phase sequencers perform the Edman degradation on peptides in much the same way as automated liquid-phase sequencers, except that the peptide is immobilized by covalent attachment to a solid support material and does not undergo cycles of solubilization and precipitation. Reagents and solvents are unidirectionally pumped through a column of bound peptide as required. In this type of sequencer the sample peptide first must be covalently linked to the support material. Several methods have been reported for achieving this task. The most reliable coupling procedures utilize the $\epsilon$-amino group of lysine, as disclosed by Laursen, R. A., et al., FEBS Lett. 21:67–70 (1972), or a C-terminal homoserine, as disclosed by Horn, M. J., et al., FEBS Lett. 36:285–288 (1973). Coupling yields are usually up to about 80% but the peptide must contain lysine or a C-terminal carboxyl group, as disclosed by Previero, A., et al., FEBS Lett. 33:135–138 (1973). The two types of solid supports for covalent coupling generally used are polystyrene, as disclosed by Laursen, R. A., Eur. J. Biochem. 20:89–102 (1971), and porous glass, as disclosed by Wachter, E., et al., FEBS Lett. 35:97–102 (1973). Both are highly substituted with functional groups and inert to the reagents and solvents used in sequencing. Small peptides containing lysine are usually attached to aminopolystyrene by the diisothiocyanate coupling procedure. Peptides without lysine are attached to triethylenetetramine resin by carboxyl activation. Large peptides and proteins are affixed to amino glass supports after activation with diisothiocyanate, as disclosed by Laursen, R. A., Solid Phase Methods in Protein Sequence Analysis, Pierce Chemical Company (1975).

After peptide attachment the resin is washed and packed into a small glass column. The reaction column is then placed into a heated holder in the sequencer. From this point, the solid-phase instrument follows much the same chemical procedure as the manual and spinning cup methods except that a wider range of reagents, buffers and solvents can be passed through the column without fear of washing out the covalently bound peptide. The routinely used solid-phase sequencing chemicals are PITC (5% V/V in acetonitrile), pyridine:N-methylmorpholinium trifluoroacetate buffer (2:3 V/V), and trifluoroacetic acid. Ethylene dichloride and methanol are used as solvents. Fractions of the ATZ-amino acids are collected in a fraction collector and later converted to the PTH-amino acid derivative either manually or automatically as described before.

The solid phase sequencer using covalent immobilization of the test protein has never achieved widespread commercial acceptance. This is predominantly the result of the nature of the covalent immobilization, which requires specialized conditions for each polypeptide and results in protein losses.

The gas phase sequencer is related to the solid phase sequencer in that it uses preimmobilized polypeptide. However, rather than avoiding peptide loss by covalent immobilization, this system uses a gaseous form of the alkaline buffer coupling reagent to avoid elution of non-covalently adsorbed peptide. The gas phase sequencer has enjoyed considerable commercial success, supplanting both the spinning cup and solid phase sequencers.

An early version of a gas phase sequencer is described in U.S. Pat. No. 4,065,412. A commercial sequencer based upon the system described in that patent is sold by Applied Biosystems of Foster City, Calif. In that system, the protein or peptide is noncovalently deposited on a glass fiber disc which contains a protein extender (Polybrene). The protein and extender form an immobilized film in the glass fiber disc which is held in a small glass chamber. Gas and liquid Edman reagents enter through a small opening at the top of the chamber and exit through the bottom.

The coupling reagent is added in an organic solvent (heptane) that will not dislodge the peptide. The coupling reaction occurs after wetting of the entire surface of the glass disc with the coupling reagent solution and drying off the organic solvent. The reaction is started by introducing the gaseous coupling base, trimethylamine (TMA). The vapor stream of coupling base and water vapor increases the pH of the protein film. In contrast to the spinning cup sequencer, the sample chamber is small and simple. Since there is no liquid buffering solution, certain peptides may be sequenced without covalent attachment. However, this requires that the coupling reagent be added in an organic solvent and that the coupling base be introduced in a separate step. Furthermore, a disadvantage of using the gaseous coupling base is that the reaction is not as easily controlled as with a liquid buffer solution. In solution, the optimum pH is approximately 9.0. At a pH higher than 9.5, the coupling reagent begins to react more rapidly with water to form byproducts (anilide and diphenylthiourea). At higher pH levels, breakdown of the peptide or protein can become a problem as set forth in the aforementioned U.S. Pat. No. 4,065,412. To affectively control the pH on the reaction surface the flow rate of the gaseous phase must be precisely controlled as well as the concentration of base (TMA, for example) in the gaseous atmosphere. This requirement for precise control of flow rates and concentrations results in a very complex and expensive instrument that requires highly skilled operators. Total instrument temperature control is needed to ensure precisely calibrated reagent aliquots.

Another disadvantage of the gas phase system is that it requires the use of Polybrene, typically in amounts of 1–2 mg, to retain the protein on the small glass disc. Polybrene also retains byproducts more efficiently, however. It has been reported by Strickler, J. E., et al., Anal. Biochem. 140:553–566 (1984), that covalently linked peptides when sequenced in a gas phase sequencer without using Polybrene produce much less of the byproduct peak. Large amounts of byproduct peaks can obscure the identification of some amino acid derivatives.

Another disadvantage of performing the reaction on the surface of the gas phase sequencer with little if any aqueous solvent is that small amounts of salts, denaturants such as urea, or buffer ions deposited from the test sample can interfere with the reaction of the alpha-amino of the N-terminal residue, or interfere with the solvent extraction of amino acid derivatives for identification or the washing out of undesired byproducts.

Another disadvantage of the gas phase sequencer is that after the coupling reaction is complete, all remaining water vapor must be removed by an inert gas drying. The byproducts are then removed by flowing an organic solvent through the disc holding chamber. It is important that the flow of solvent be precisely controlled so as not to dissolve or dislodge any immobilized protein. Since the flow is in one direction only and there is no film reforming step in the process, any dissolved peptide is lost in the wash.

It is known to prepare test samples for amino acid sequencing by separating polypeptides from one another or from contaminants through the use of dialysis membranes or high pressure liquid chromatography. However, such procedures have not been incorporated into amino acid sequencing devices, and in fact are considered undesirable because they result in the loss of sample.

These and other problems and disadvantages are addressed by the present invention.

SUMMARY OF THE INVENTION

It has now been discovered that amino acid sequencing can be performed in a system in which separation of the peptide from system reactants and from cleaved terminal amino acids during the sequencing protocol is achieved by the principles of adsorption chromatography, in a manner which maintains the separability during successive cleavages and repetition of the protocol without loss of the peptide through desorption. Through use of such a system, one avoids the need for covalent bonding or any other type of bonding or irreversible immobilization of the peptide to a solid phase.

The peptide is immobilized on an adsorption column by virtue of the adsorption properties of the peptide. The peptide is preferentially absorbed relative to other components of the system due to the greater strength of the adsorptive interaction of the peptide with the column absorbent. This preferential absorption is attributable to the size of the peptide and the number of amino acids forming the peptide. In some cases, the preferential adsorption is also attributable to the type of interaction between the peptide and the absorbent.

Once the peptide is loaded onto the column, the various components of the sequencing protocol are passed into or through the column in either the liquid or gaseous phase for contact with the adsorbed peptide in accordance with the protocol. The passage of components through the column in any single cycle of the protocol, i.e., for the removal of a single terminal amino acid, includes flows in both directions. As a result, migration of the peptide in one direction along the length of the column due to desorption and readsorption during the passage of one such component is compensated by migration in the reverse direction during the passage of another such component subsequent to the first. The components may include reactants or other treatment agents, solvents, buffer solutions, or wash liquids.

The process is repeated for each cycle of the protocol, i.e., for the cleavage of each successive amino acid, to result in a minimal net migration or band broadening of the remaining adsorbed peptide along the length of the column, and in certain cases, to result in no net migration but instead a focusing or band narrowing of the remaining peptide. In certain embodiments of the invention, each cycle contains two or more such reversals in flow direction.

In preferred embodiments of the invention, the stationary phase of the adsorption column contains two solid adsorbents in fluid communication with each other but differing in adsorption characteristics. One adsorbent is concentrated at one end of the column, and the other concentrated at the other end. In preferred embodiments, the column is divided into two contiguous zones, serially arranged in tandem (i.e., lengthwise along the column), one adsorbent occupying each zone.

The adsorption characteristics of the two adsorbents in these embodiments differ to the extent that the partitioning of the peptide between the mobile and stationary phases differs. In addition, various mobile phases are used in the procedure, and certain of these mobile phases result in a greater adsorptive attraction of the peptide for one adsorbent than for the other, while certain others have the reverse effect, causing the peptide to have a greater adsorptive attraction for the second adsorbent than the first.

The flow directions of the components during a cycle of the protocol are then selected such that at least one mobile phase of each type is passed into or through the column in such a direction that mobile phase first contacts the adsorbent where the partitioning will result in relatively weaker peptide adsorption and then flows toward the other adsorbent. Peptide adsorbed in that first zone will therefore tend to migrate in the direction of the flow due to the desorption effect of the mobile phase. The species will have a lesser or no effect on peptide adsorbed in the other zone, however, which is positioned downstream relative to the first zone according to the direction of flow. Since the flow direction is dictated by the character of the mobile phase, the analogous behavior occurs with flow in the opposite direction, both directions causing flow toward the interface between the two adsorbent zones. Migrations beyond the interface will occur, but to a lesser extent. Over the course of a cycle of the protocol, this interface-directed migration compensates at least in part for any migration occurring in directions away from or across the adsorbent zone interface at other points in the cycle. Over the course of a succession of repeated cycles, peptide residing in either adsorbent zone will migrate toward the interface between the two adsorbent zones.

The selection of adsorbent for use in the practice of the present invention will be limited to those for whom peptides or proteins whose amino acid sequences are to be determined in accordance with this invention have adsorption affinity. In the case of the two-adsorbent systems of the preferred embodiments of this invention, the peptides will have adsorption affinity for at least one of the two adsorbents, and in many cases both, although possibly to different degrees. In particularly preferred two-adsorbent systems, the adsorbents will be selected such that the collective adsorption affinity of both adsorbents will extend to a wide range of proteins and peptides, and that adsorption affinity will be retained as the peptide or protein is successively degraded by sequential cleavage and removal of amino acids from one end.

Any two components which are used in succession in the sequencing protocol can serve as the alternating flow species, provided they are appropriately selected in terms of their adsorption affinities and direction of flow. In preferred embodiments of the invention, however, the first such component is a reactant or a carrier liquid carrying a reactant at one stage of the protocol, and the second such component is a wash liquid or solvent passed through the column subsequent to the reaction to remove excess reactant, the cleaved amino acid or both. In such embodiments, the wash liquid or solvent causes a compensating migration of the peptide in the direction opposite that of the migration occurring during contact with the reactant.

Other features, advantages and preferred embodiments of the invention will be apparent from the description which follows.

DETAILED DESCRIPTION OF THE INVENTION AND PREFERRED EMBODIMENTS

The present invention is generally applicable to protocols in which the amino acid sequences of proteins or peptides are determined by repeated cycles which involve coupling a coupling agent to a terminal amino acid followed by cleavage of the coupled amino acid from the peptide chain. For simplicity of description, the term "peptide" is used herein to include both peptides and proteins. The invention is particularly well adapted to the Edman procedure set forth above in the Background of the Invention. For ease of understanding, the description which follows will address specific methods of applying the present invention to the Edman procedure. This is done with the understanding however that with appropriate modifications which will readily occur to those skilled in peptide sequencing, the invention is also applicable to modifications of the Edman procedure and to other sequencing procedures which include the same or similar steps.

Figure 1:
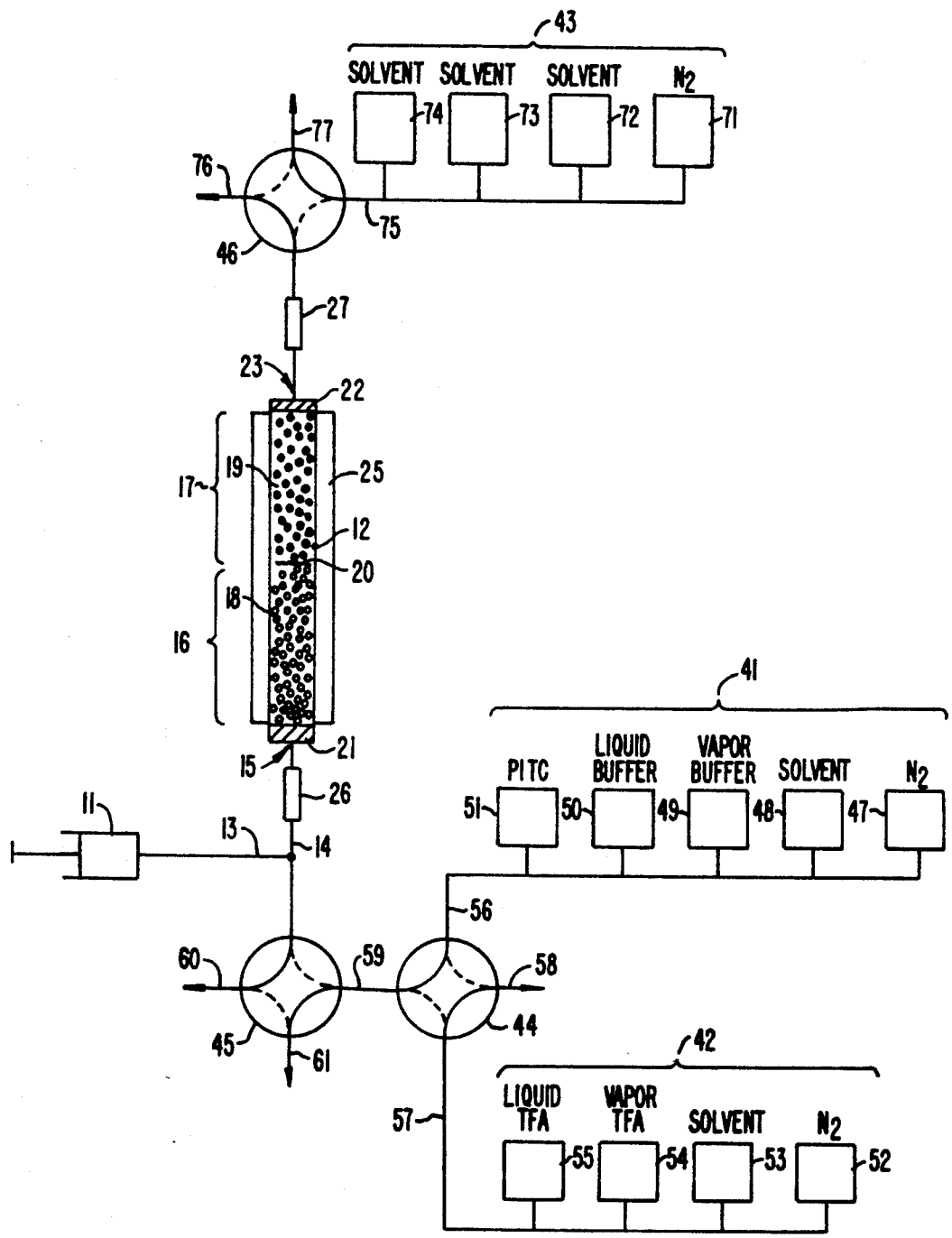
FIG. 1 is a schematic representation of a sequencer useful in the practice of the invention, containing an adsorption column with two adsorbent zones and capable of the passage of fluid in both directions.

FIG. 1 illustrates a sequencer system suitable for use in the present invention. The peptide to be sequenced is supplied by a syringe 11 to a vertically mounted flow-through adsorption column 12. Upon leaving the syringe, the peptide travels through a supply line 13 to a lower flow line 14 leading directly to an entry port 15 at the lower end of the column. The column 12 is preferably a packed tube, the tube being of a material which is transparent to light, such as glass, for example. The internal volume of the tube is not critical and may vary widely. One example is a glass tube having an internal volume of about 0.2 mL or less, packed with about 20 mg to about 40 mg of adsorbent, on a dry basis.

Noting once again that FIG. 1 represent a preferred embodiment, of the invention, the adsorbent in the adsorption column 12 in this drawing is divided into two zones 16, 17, each zone containing an adsorbent material 18, 19 differing in adsorptive properties from the adsorbent material of the other zone. The adsorbents in this embodiment are particulate solids forming a fixed bed in the column interior. Free passage of fluid occurs within each zone and across the interface 20 between the two zones.

The adsorption characteristics of the two adsorbents may differ in a variety of ways by appropriate selection of the functional groups on the adsorbents. Prominent examples of adsorbent pairs are pairs whose members differ by surface electrostatic charge and those whose members differ by hydrophobicity. Within each such class of adsorbent pairs, a wide range of chromatographic media may be used. Adsorbent pairs of the first class may for example be anion and cation exchange supports for high-performance liquid chromatography (HPLC), such as Synchropak AX300, Synchropak Q300, Synchropak CM300, and Synchropak S300. Adsorbent pairs of the second class will include hydrophilic and hydrophobic resins. Examples of hydrophilic resins are controlled pore glass and unsubstituted silica, and examples of hydrophobic resins are ($C_4$–$C_{18}$ alkyl)-substituted silicas, preferably ($C_8$–$C_{18}$ alkyl)-substituted silicas, and various hydrophobic polymeric resins.

In the embodiment illustrated in FIG. 1, the lower adsorbent 18 is a hydrophilic resin such as a typical normal phase HPLC medium and the upper adsorbent 19 is a hydrophobic resin such as a typical reverse phase HPLC medium. The hydrophilic resin has a relatively high affinity and long retention time for hydrophilic groups on peptide molecules and a low affinity and short retention time for the hydrophobic side products of the reactions of the Edman procedure.

Examples of controlled pore glass hydrophilic resins are those available from Electro-Nucleonics, Inc., of Fairfield, N.J., and examples of unsubstituted silica hydrophilic resins are those bearing the trade name Nu-Gel, available from Separation Industry, of Metuchen, N.J. A specific example of the latter is Nu-Gel 952 AC, with an average pore size of 200 Angstroms, and a particle size of 200–400 mesh. The volume of lower adsorbent is not critical and may vary widely. A typical volume is 0.1 mL.

Examples of reverse phase HPLC resins suitable for use as the hydrophobic resin are Synchroprep coupled silicas, which are ($C_8$–$C_{18}$ alkyl)-substituted silicas, available from SynChrom, Inc., of Lafayette, Ind. A specific example is one having an average pore size of 300 Angstroms and an average particle size of 30 microns. Here again, the volume of the resin used is not critical and may vary widely, a typical volume being 0.1 mL.

While two-zone stationary phase systems are preferable because of their ability to focus the peptides at the zone interface as described below, it should be understood that a single-zone phase, preferably of the hydrophilic type, may also be employed, with bidirectional flow.

Peptides have adsorption affinity for either hydrophobic solid phases, hydrophilic solid phases, or both, depending on the peptide, or acquire such affinity when denatured. The peptide whose amino acid sequence is being determined will therefore be immobilized by either or both of the two resins in this embodiment, without covalent bonding but instead by reversible non-specific adsorption. When an aqueous solution flows through the column in the upward direction (first contacting the lower resin 18 which is hydrophilic and moving toward the upper resin 19 which is hydrophobic), peptide present in the solution will come to rest on the upper resin due to the attraction between the peptide and the hydrophobic groups on the resin and the lack of attraction between those hydrophobic groups and the aqueous carrier. Likewise, peptide already adsorbed on the column from previous stages of the procedure will migrate no further than the upper hydrophobic resin, or at least at a lesser rate through the hydrophobic resin than through the hydrophilic resin. This extends to all aqueous solutions, including aqueous wash solutions as well as aqueous solutions of proteins and hydrophobic peptides which include high concentrations of salts and other denaturants such as urea, sodium dodecyl sulfate (SDS), and sucrose. Conversely, when organic solvents and organic solutions flow through the column in the downward direction (first contacting the upper hydrophobic resin 19 and flowing toward the lower hydrophilic resin 18), peptide already adsorbed on the column from previous stages of the procedure will migrate no further than the lower hydrophilic resin. Organic solvents and solutions will typically be used, for example, during organic solvent extraction of excess reagent, reaction by-products and the ATZ-amino acid, which is the terminal amino acid after cleavage from the peptide and still in its coupled form.

The adsorbent or adsorbents may be of any geometry capable of retaining adsorbed peptide as liquid or gaseous agents flow past. In preferred embodiments of the invention, the adsorbent or adsorbents are in the form of a bed of solid particles filling the interior of the column. The preferred bed is a fixed bed held in place by a suitable retaining barrier or plug at each end which permits passage of fluid. FIG. 1 illustrates porous plugs 21, 22 serving this function. Examples of suitable materials for such plugs are glass and Teflon wool. The column itself may be of any configuration or orientation. Straight vertical columns are particularly convenient.

Fluid passes upwardly into the column 12 through lower port 21 and leaves through upper port 23 communicating with an upper fluid flow line 24. Both column ports 15 and 23 are fluid tight. The column in this embodiment also includes a coolant jacket 25 for temperature control during the sequencing procedure. Releasable fittings or couplings 26, 27 of conventional construction and configuration are installed in the fluid flow lines for ready engagement and disengagement between the column 12 and coolant jacket 25 on the one hand and the remaining components of the system and apparatus on the other. The column 12 and coolant jacket 25 may thus be constructed as a cartridge which may be removed from the apparatus after the completion of a sequencing procedure and replaced with a clean cartridge for each run to avoid cross contamination of peptides.

Figure 2:
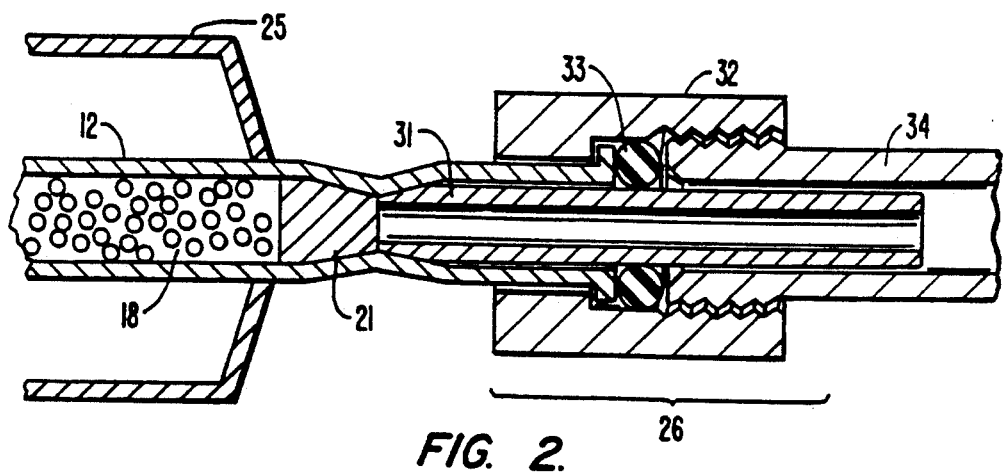
FIG. 2 is a cutaway view of one end of a column cartridge suitable for use in the sequencer of FIG. 1.

One example of a construction for the column and releasable coupling is shown in FIG. 2. The coupling illustrated in this drawing is the lower coupling 26, although the upper coupling 27 may be of identical construction.

The column 12 in FIG. 2 is a glass tube 2 mm in inner diameter. Near its lower end, the glass tube is crimped so that a length of small bore (1.5 mm) Teflon tubing 31 is received and retained inside in a tight fit, with a portion of the tubing extending beyond the lower end of the glass tube. An internally threaded sleeve 32 surrounds the end of the glass tube and covers part of the protruding portion of the Teflon tubing. An O-ring 33 is positioned at the end of the Teflon tubing 31 for compression between it and the end of the glass tube. A mated element 34 at the terminus of the fluid flow line to which the column is to be coupled forms the male portion of the releasable coupling. This mated element 34 is externally threaded to mate with the internal threads on the sleeve 32, which serves as the female portion of the coupling. When the male and female portions are joined together and tightened, the O-ring 33 is compressed to form a fluid-tight seal. Alternative means of holding the male and female portions together, such as those involving spring tension, will readily occur to those skilled in the art.

Returning to FIG. 1, the system includes two reservoir blocks 41, 42 at the bottom of the column leading to the lower inlet 15, one additional reservoir block 43 at the top of the column leading to the upper inlet 23, and three four-way valves 44, 45, 46. Each reservoir block contains a series of reservoirs or sources of materials or components used in the Edman procedure. For example, the first block 41 of the two reservoir blocks at the bottom of the column includes a source of pressurized inert gas 47, a reservoir containing solvent 48, a reservoir containing vapor or volatile buffer (used in forming the base for the coupling reaction) 49, a reservoir containing liquid buffer (also used in forming the base for the coupling reaction) 50, and a reservoir containing the coupling reagent (PITC) 51. The second block 42 at the column bottom includes a source of pressurized inert gas 52, a solvent reservoir 53, a reservoir containing cleavage reagent TFA in vapor form 54, and a reservoir containing cleavage reagent TFA in liquid form 55.

Exit lines 56, 57 from these two lower reservoir blocks 41, 42, respectively, both lead to a common four-way valve 44. Of the two remaining ports of the four-way valve, one leads to waste 58 and the other 59 leads to the second four-way valve 45. Of the three remaining ports of the second four-way valve 45, one leads to the fluid flow line 14 which in turn leads to the lower column port 15, another 60 is for removal of the cleaved ATZ-amino acid for identification, and the third 61 leads to waste.

The upper reservoir block 43 contains reservoirs for pressurized inert gas 71, and for a series of organic solvents 72, 73, 74 for use in various stages of the procedure. These may for example include a reservoir of acetonitrile 72, a reservoir for ethyl acetate 73, and a reservoir for benzene 74. In this and the other two reservoir blocks 41, 42, the inert gas reservoir may be separated from the other reservoirs by high-pressure valves, and all other reservoirs may be isolated from each other by appropriate valves, none of which are shown in the drawing.

The output line 75 from the upper reservoir block 43 is directed to the upper four-way valve 46 which in turn directs fluids from the reservoir block to the upper fluid flow line 24 and hence to the upper port 23 of the column. Of the two remaining ports on the upper four-way valve 46, and 76 is used for removal of excess reagent flowing upward through the column, and the other 77 is directed to waste.

The description which follows is an illustrative methodology for use of the system depicted in FIGS. 1 and 2 in performing an Edman procedure. The methodology is illustrated on a molecular scale in FIGS. 3a-3e. This description illustrates but one example. Modifications and substitutions which can be made within the same methodology or which would be made for the purpose of converting the methodology to other procedures for sequential peptide degradation will be readily apparent to those skilled in the art.

METHODOLOGY

Step 1—Peptide Loading

Figure 3A:
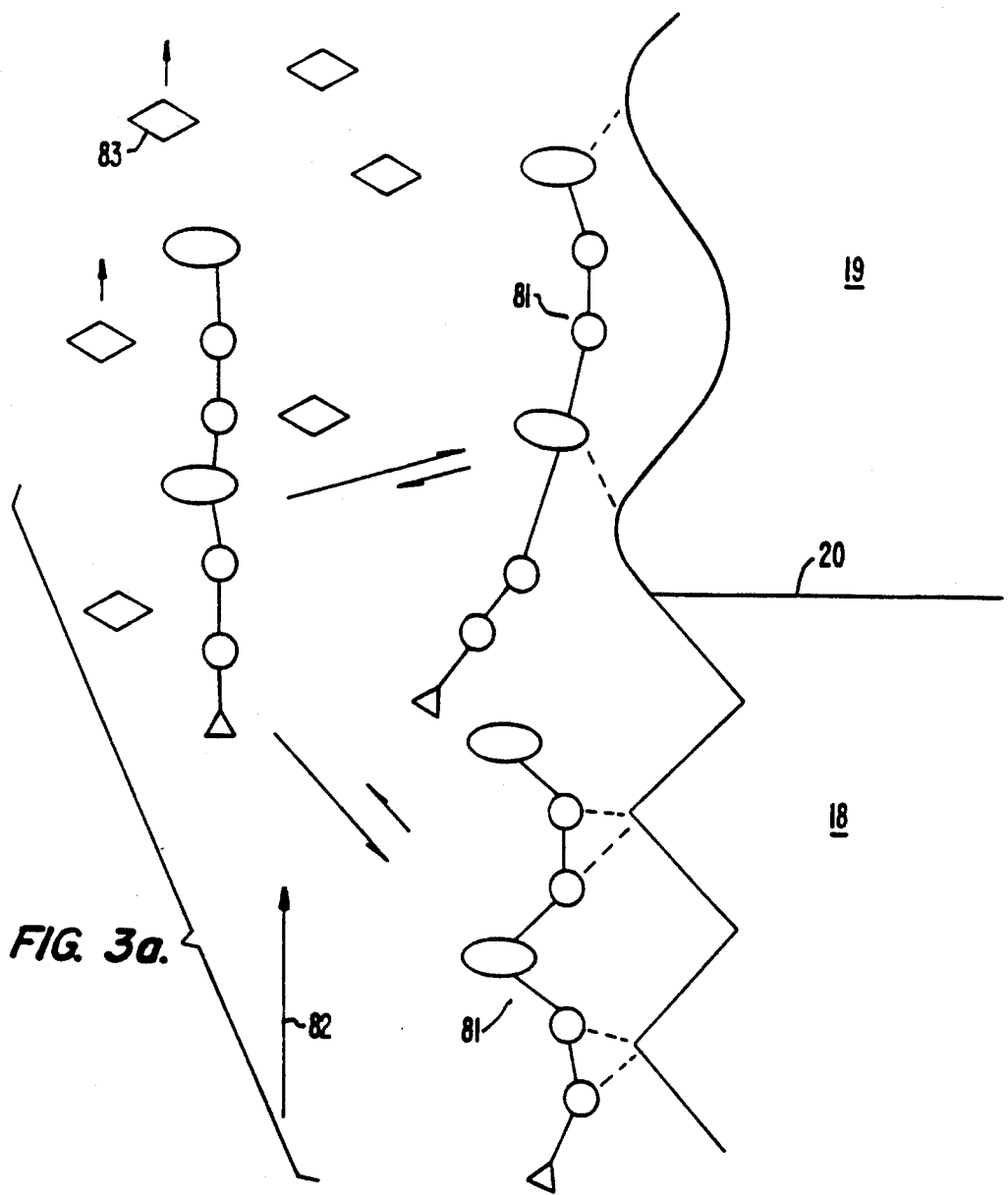
FIGS. 3a-3e illustrate one method of performing the Edman sequential peptide degradation procedure using the sequencer of FIG. 1.

The chemistry of this step is illustrated in FIG. 3a. Referring to FIGS. 1 and 3a together, peptide 81 from the syringe 11, preferably in an aqueous solution, is loaded onto the column 12 from the bottom, through the lower column port 15, flowing upward as indicated by the arrow 82. Most proteins and some peptides will be retained by the hydrophilic adsorbent 18. If the protein is in a high concentration of salt or denaturant, it may elute from the hydrophilic adsorbent and migrate up into the hydrophobic adsorbent 19, where it will be retained. In any case, low molecular weight components 83 will pass through and elute from the column. The solution that passes through the column may be collected from analysis to verify that all of the protein is retained by the column.

At this point in time, the four-way valve 46 at the top of the column is in a by-pass position such that excess solution passing up through the column is collected at line 76. Solvents from the upper reservoir block 43 which are flowing through the reservoir block output line 75 are vented to waste through the waste port 77.

In typical operation, the hydrophilic and hydrophobic adsorbents 18, 19 are flooded with aqueous peptide solution so that the peptide in the solution migrates upwardly through the column but is retarded by the hydrophobic adsorbent 19. Although it is preferable to load the peptide on the column from the bottom, the peptide may also be loaded from the top.

Step 2—Upward Wash

In this step, a wash liquid is injected into the column to remove salts, denaturants, free amino acids and small unwanted peptides which were present in the peptide sample. The wash liquid may be water or aqueous acetonitrile at a low concentration, and the direction of flow is preferably upward. For upward flow, the wash solution may be supplied from the syringe 11 used for the peptide sample, and will flow upwardly through the column 12 and pass out of the system through the excess reagent port 76 of the upper four-way valve. Step 1, Step 2 or both may be performed either manually or by automated instrumentation, and they may be performed either in the sequencer instrument (i.e., with the column in place as shown in FIG. 1) or separately from the sequencer instrument (by first disconnecting the releasable couplings 26, 27 and removing the column as a cartridge) and stored for subsequent sequencing.

Step 3—Loading of Coupling Agent

Figure 3B:
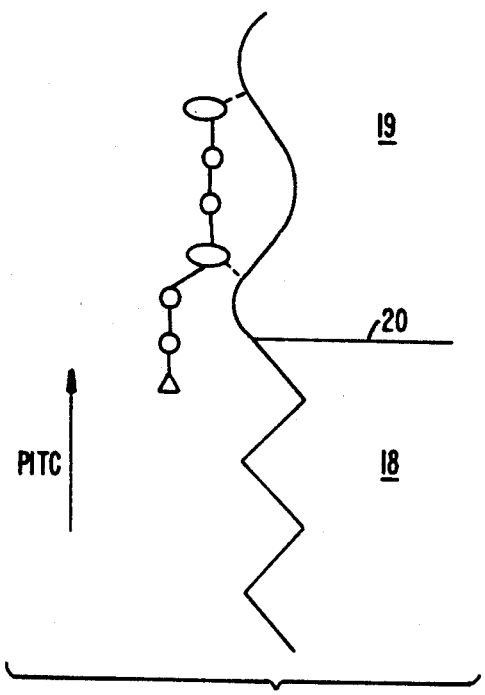

This step is illustrated in FIG. 3b. Coupling agent such as PITC is delivered to the column in a suitable solvent such as, for example, acetonitrile or heptane, from the PITC reservoir 51. A preferred form of delivery is a 2% solution of PITC in heptane.

One method of delivering the PITC to the column is to first place the two four-way valves 44, 45 in the positions shown in FIG. 1, and to direct the PITC solution through these valves, thereby filling the volume of the line 59 between the two valves and directing the excess to waste 61. The positions of the two valves are then changed simultaneously and inert gas (such as, for example, nitrogen) from source 52 of block 42 is directed through the valves. This will result in passing PITC into the column 12 in a precisely controlled amount corresponding to the total of the internal volumes of the connecting line 59 and of the second four-way valve 45. As this controlled amount of the PITC solution enters the column, PITC solution occupying the interior of four-way valve 44 is washed out of the valve by passing inert gas (for example, nitrogen) from the inert gas source 47 in the first reservoir block 41 through the valve 44 and subsequently out through the waste line 58. This method may be termed a loop method since it involves the purging of a length of tubing with the PITC solution to obtain a precisely controlled volume of the solution before directing that volume to the column.

As an alternative to the loop method, the four-way valves 44, 45 may be positioned to deliver the PITC directly from the reservoir 51 to the column 12. This technique offers less control of the volume of PITC passed into the column, and when a non-polar species is used as the solvent in the PITC solution, a large flow of the solution may result in peptide migrating upward inside the column toward the top. The degree to which this raises a risk of the peptide migrating out of the column will depend on how strongly the peptide is retained by the hydrophobic adsorbent, which in turn will depend on both the peptide itself and the solvent used for the PITC solution. For peptides which are adsorbed by the hydrophobic adsorbent, it is preferable when using this technique to use heptane as the PITC solvent rather than acetonitrile. This will avoid elution of small peptides from the hydrophilic zone into the hydrophobic zone when a large amount of PITC solution is inadvertently used.

Regardless of which of these two procedures is used, it is preferable to subsequently remove all solvent from the adsorbent by a flow of inert gas either from the top or bottom of the column from either of the three sources 47, 52 or 71, leaving the PITC on the adsorbent. This, however is optional.

Step 4—Loading of Coupling Base

FIG. 3b illustrates this step as well, in which the base to be used in association with the coupling agent is delivered to the column in a manner analogous to that of Step 3. The base is supplied in the form of a buffer.

The loop method of Step 3 can be used to deliver a small precisely controlled amount of liquid buffer from the liquid buffer reservoir 50, thereby protecting against an excessive amount of buffer solution being passed through the column which may carry small peptides up the column. As in the method of Step 3, the loop is purged with buffer from the first reservoir block 41 with excess buffer flowing out the waste port 61. This is followed by switching the two four-way valves 44, 45, and purging the loop with nitrogen from the inert gas reservoir 52 in the second reservoir block 42. The liquid buffer may be combined with volatile buffer (such as, for example, trimethylamine or triethylamine in water) from the volatile buffer reservoir 49.

When the total amount of liquid delivered in this manner is too small to entirely wet both adsorbents, the peptide will migrate upwardly through the column but not out of the adsorbent zones. If the peptide is of such a nature that it will be strongly adsorbed on the hydrophobic medium, an amount of liquid buffer that exceeds the volumetric capacity of the adsorbent zones may be used.

In an alternative method, the four-way valves 44, 45 may be manipulated in a manner which uses the loop and yet supplies a greater volume of base than does the loop method. According to this method, the loop is first purged with the buffer as in the loop method. Then, for a short period of time such as two seconds, the downstream four-way valve 45 alone is shifted to direct the liquid buffer upwardly through line to the column as it leaves the loop while the loop is still being purged with the buffer. The upstream four-way valve 44 is then shifted to isolate the loop from the buffer reservoir while passing inert gas from the inert gas source 52 in the lower reservoir block 42 through the loop, thereby forcing the buffer in the loop through the downstream four-way valve 45 and fluid flow line 14 into the bottom of the column. This timing can be adjusted so that sufficient liquid buffer enters the column to wet the both adsorbents and so that excess buffer passes through the column and out the top.

Suitable bases for this step of the procedure will be those which control the pH to a level within the range of 8-10 and which dissolve both the peptide and the PITC. Examples of suitable coupling bases are hydrophilic solutions of DMAA, DMBA, or the like, preferably with a propanol content lower than that present in conventional sources of these products (for example, 5-20% or less). Hydrophilic solutions of this type typically cause moderate migration of the peptides upwardly through the hydrophilic adsorbent but very slow migration at best through the hydrophobic adsorbent.

This system permits the use of high volumes of liquid buffer which results in precise pH control and consequently an increased efficiency of the coupling reaction. If desired, the liquid buffer can also contain detergents such as SDS to help solubilize the protein. Another reagent that may be included is Norleucine, a primary amine similar to natural amino acids, which may be used as an internal standard and carrier-scavenger for PTC-amino acid.

Although Steps 3 and 4 are described in terms of sequential addition of coupling reagent and coupling base, it is only important to the reaction that the two reagents be in simultaneous contact with the peptide. Thus, the system can be operated by combining Steps 3 and 4, thereby applying both coupling reagent and coupling base in a single addition.

Step 5—Solvent Removal

In this step, the solvent or solvents in which the coupling reagent and coupling base were supplied to the column are removed by a flow of inert gas.

In a preferred technique, the gas is first passed through the column in the upward direction so that the aqueous liquid remaining on the column from the previous step flows upward toward the hydrophobic material. This may be accomplished by passing inert gas 47 from the first of the two lower reservoir blocks 41 through both lower four-way valves 44, 45 into and through the column. Then, after most of the liquid is removed, the drying may be completed by high pressure inert gas 71 from the upper reservoir block 43 directed through the upper four-way valve 46 and downward through the column 12, with the lower four-way valve 45 directing the column outflow to waste.

Complete removal of water is desirable but is not as critical as in prior techniques such as the spinning cup sequencer and gas sequencer described above. When organic solvent is passed downwardly through the column in succeeding steps according to this procedure, water which has not been removed from the column during Step 5 may, upon mixing with the organic solvent, modify the partitioning of the peptide between the stationary and mobile phases during those succeeding steps. Such a modification may increase the tendency of the peptide to migrate downwardly in the hydrophilic adsorbent zone, away from the interface between the zones. Such migration will be counterbalanced, however, by subsequent steps of the procedure which involve an upwardly flowing aqueous liquid buffer.

During downward movement of the high pressure gas through the column, any coupling reagent or base remaining in the four-way valve 44 may be washed out by solvent from the solvent reservoir 48, the solvent then being passed to waste 58.

Step 6—Downward Wash

Figure 3C:
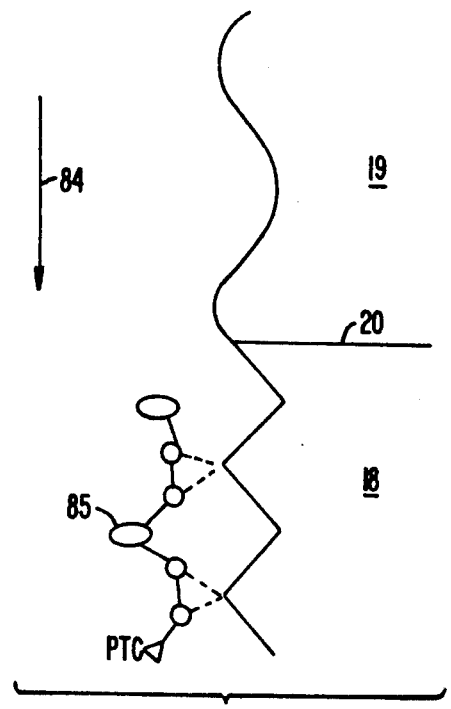

This step is illustrated in FIG. 3c.

In this step, an organic solvent is passed through the column in a downward direction, as indicated by the arrow 84, to remove non-volatile side products and remaining buffers from the column, leaving the PTC-peptide 85 adsorbed on the column. Solvents useful in this wash range from very non-polar solvents such as heptane and benzene to solvents of more moderate polarity such as ethyl acetate and acetonitrile. The solvent is supplied by an appropriate reservoir 72, 73, 74 in the upper reservoir block 43, enters the column from the top and flows downwardly to exit the column at the bottom. Solvents are preferably pressurized to about 10 psi to about 100 psi by conventional means, such as by pressurized inert gas from the inert gas reservoir 71, for passage through the column. The reservoir block will typically have valves capable of withstanding pressures of up to 100 psi from the inert gas source 71 so that high pressure inert gas can flow through the column to compress any gas bubbles that may trap reaction by-products or reagents.

Step 7—Cleavage Reaction

Figure 3D:
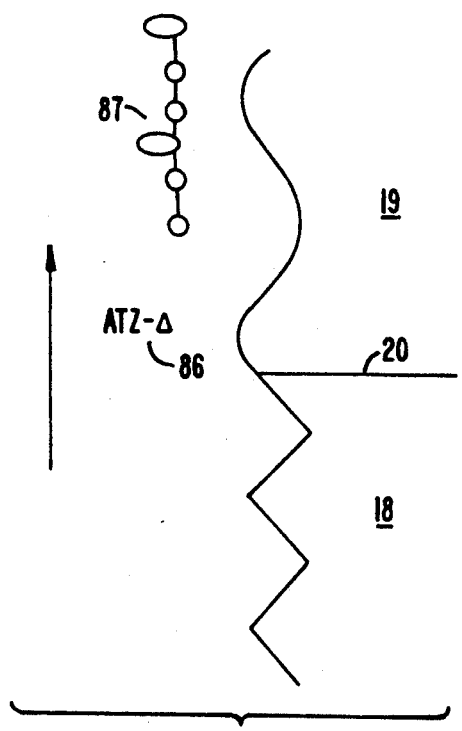

In this step, which is illustrated in FIG. 3d, the coupled (PTC-) peptide is cleaved with a cleavage acid. Cleavage acids suitable for use in this reaction are anhydrous and volatile and of pH sufficiently low to cause cleavage of the PTC-peptide into the ATZ-amino acid 86 and a peptide of one less amino acid 87. Cleavage may be performed with either a liquid acid (such as for example HFBA, TFA, or PFFA, in an anhydrous solution of acetic acid or acetonitrile), an acid vapor or a combination of both. Liquid acids increase the kinetics of the reaction. Gaseous acids, however, reduce the risk of elution of the peptide off the top of the column. Thus, the liquid acid is preferred for short reaction times where the peptide is relatively large and the risk of elution from the column is relatively small. The system may operate with liquid acid at the beginning stages of sequencing and with a gas phase acid at the later stages when the length of the peptide chain has been substantially reduced.

When using vapor-phase acid, acid vapor from the acid vapor reservoir 54 in the second reservoir block 42 passes through the block exit line 57 and the two four-way valves 44, 45 to the fluid flow line 14 at the column base, and up through the column 12. Liquid-phase acid flows through the same flow path.

The cleavage reaction is preferably performed at a temperature of 10° C. to 50° C. The reaction temperature may be controlled by the temperature of the circulating coolant in the coolant jacket 25. The reaction is quenched by the removal of excess liquid or gaseous acid from the column by an upward flow of inert gas followed by high pressure downward flow as described above. The method of this invention permits one to remove the acid to a more complete degree than does either the gas phase or spinning cup sequencers of the prior art. This is because the extraction of the ATZ-amino acid from the remaining peptide by chromatographic separation which occurs in Step 8 below can be done with a solvent which is more polar than any which can be used in either the gas phase or spinning cup prior art systems. As a result, the extraction in this invention does not require a small amount of remaining acid as in these prior art techniques.

Step 8—Extraction of ATZ-Amino Acid

Figure 3E:
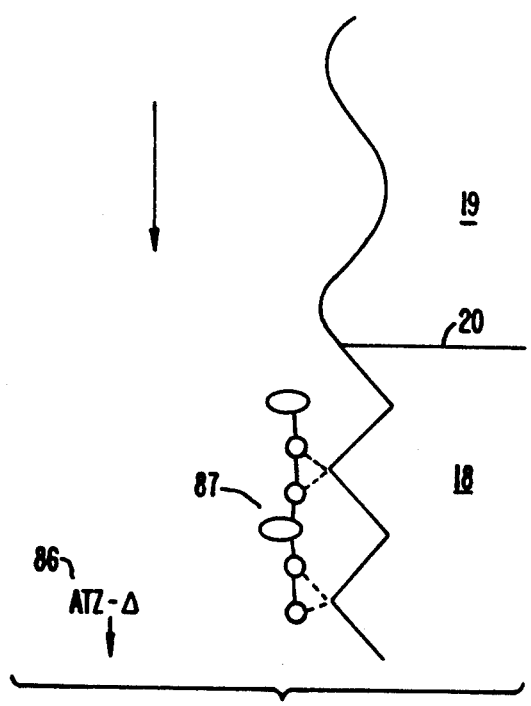

In this final stage, as represented by FIG. 3e, the cleaved ATZ-amino acid 86 is extracted with a suitable organic extraction solvent such as ethyl acetate or acetonitrile. The solvent will be one which provides complete elution of all ATZ-amino acids but only a relatively small degree of migration of free peptide through the resin.

As illustrated, solvent from solvent reservoir 73 is passed through the upper four-way valve 46 and through line 24 downwardly through the column 12, then through the lower four-way valve 45 nearest the column and out the exit port 60, from which the solvent, now carrying the ATZ-amino acid, is directed to a suitable reaction vial (not shown) for subsequent reaction and identification. In such a vial, the cleaved ATZ-amino acid in solvent is converted to the stable PTH amino acid in a conventional manner. As is typical, the vial can contain, or have added to it, an aqueous solution of TFA for the aqueous acid conversion. After conversion of the ATZ-amino acids to PTH-amino acids by reaction with dilute acid in the conventional Edman manner, the residues can be identified by conventional procedures, notably those involving liquid phase chromatography.

After the solvent flow, an inert gas is passed through the column in the manner described above to remove any remaining organic acid. The column is then ready for repetitions of the sequencing procedure for cleavage of successive ATZ-amino acid derivatives from the remaining peptide which remains adsorbed on the column.

A major advantage of the method of the present invention is its ability to avoid covalent attachment of the peptide to a solid phase and yet to avoid loss of the peptide from the system during the wash steps. The liquids used in the various stages of any one cycle of the procedure are chosen such that at least some of the liquids cause migration of the peptide in the direction of flow. By using alternating flow directions, migrations of the peptide in one direction are compensated for by subsequent migrations in the reverse direction. In the preferred systems in which the adsorbent is comprised of two serially arranged adsorbent zones each with a distinct adsorbent material differing from the other in adsorption characteristics, the two adsorbents, the liquid phases and the directions of flow are all selected such that the overall effect of the alternating flows through successive cycles of the procedure is to focus or concentrate the peptide at the interface between the two adsorbent zones. The rate at which this focusing occurs will depend upon the degree of partitioning of the peptide between the mobile phase (the various liquids passing through the column) and the stationary phase (the adsorbents).

To summarize the mechanism by which the eight-step procedure described above produces focusing of the peptide, Step 1 involves the loading of the column with a sample of peptide by upward flow. During this loading, some peptides will typically be adsorbed by the hydrophilic lower adsorbent while other peptides will pass through the hydrophilic adsorbent to be adsorbed by the hydrophobic upper adsorbent. Low molecular weight components of the sample mixture are not adsorbed by either adsorbent but instead elute from the column. During the wash and coupling steps which immediately follow (Steps 2, 3 and 4), further liquids pass upwardly through the column and any attendant migration of the peptide, or of the PTC-peptide formed by the coupling reaction, is in the upward direction. Any liquid movement and attendant migration of PTC-peptide which occurs during the drying of Step 5 is also in the upward direction due to the upward flow of inert gas in this step. With the exception of Step 3, all fluids in the steps up to this point are either aqueous or otherwise hydrophilic to the extent that the partitioning of the peptide between the mobile and stationary phases provides a significantly stronger adsorption of the peptide on the hydrophobic adsorbent than on the hydrophilic. The major portion of the peptide migration occurring to this point therefore occurs in the hydrophilic zone upward toward the interface. Migration also occurs past the interface into the hydrophobic zone, although to a lesser degree. Flow in the downward direction occurs for the first time in Step 6, in which an organic solvent is passed through the column to remove by-products and buffers. In this case, the partitioning of the peptide between the mobile and stationary phases has the reverse result, i.e., a significantly stronger adsorption of the peptide on the hydrophilic adsorbent than on the hydrophobic. Consequently, the downward flow in Step 6 tends to cause PTC-peptide adsorbed in the hydrophobic (upper) zone to migrate towards the hydrophilic zone. In Step 7, the cleavage acid (which is hydrophilic) flows into the column in the upward direction to cause migration of the peptide back towards the hydrophobic zone. Finally, the extraction of the ATZ-amino acid derivative in Step 8 is performed in a downward direction with a solvent whose partitioning effect causes greater migration of the peptide through the hydrophobic zone than through the hydrophilic zone. Accordingly, peptide adsorbed in the hydrophobic zone will once again migrate downward toward the interface. This alternating movement of the peptide between the hydrophilic and hydrophobic zones causes a focusing of the peptide near the interface between the two zones, thereby preventing escape of the peptide from the column.

In addition to the peptide focusing which results from the adsorption and peptide migration methodology of the present invention, the arrangement of feed lines and valves themselves offer several advantages. One such advantage is that the adsorption column 12 can be bypassed so that the feed lines and valves used for delivery of the system reagents to the column can be washed and the wash liquid passed directly to waste. A full purging of these lines and valves with solvent can thus be achieved without the need to pass the purging fluids through the column. This reduces the amount of solvent flowing over the adsorbed peptide during the course of the procedure, thereby reducing the risk of losing peptide by extraction from the column as well as the risk of oxidation of PTC-peptide on the column due to peroxide which may be present in trace amounts in the solvent. An additional advantage is the ability of the system to simultaneously purge the column with inert gas while the reagent delivery lines and valves are being purged with wash liquid. Solvent is thus removed from the adsorbent at the same time that excess reagent is removed from the delivery passages. This helps reduce the time required for washing between the reactive steps of the procedure. A third advantage is that for systems sized to handle very small samples the total internal volume of the valves and lines needed to deliver all reagents can be as large as the volume of the sample chamber. This provides a convenient means of achieving precisely controlled volumes of reagent prior to their introduction into the column.

The foregoing is offered primarily for purposes of illustration. It will be readily apparent to those skilled in the art that the arrangement of flow lines and valves, as well as the operating conditions, materials, procedural steps and other parameters of the system described herein may be further modified or substituted in various ways without departing from the spirit and scope of the invention.

What is claimed is:

1. A method for the cleavage and separation of a terminal amino acid from a peptide, in which said peptide is contacted with a series of fluids comprised of reagents and wash liquids, said method comprising:
   (a) adsorbing said peptide on an adsorption column containing first and second stationary phases arranged in series therein, said first and second stationary phases differing in adsorption characteristics and selected such that at least one of said stationary phases will adsorb said peptide; and
   (b) contacting said peptide so adsorbed with said fluids by passing said fluids in sequence though said column with at least one pair of said fluids being passed through said column in opposite directions,
      (i) the fluids of said pair being selected such that the partitioning of said peptide between one of said fluids of said pair and said stationary phases provides said peptide with lesser adsorption affinity for, and thereby a greater tendency for migration in, said first stationary phase than said second, and the partitioning of said peptide between the other of said fluids of said pair and said stationary phases provides said peptide with a lesser adsorption affinity for, and thereby a greater tendency for migration in, said second stationary phase than said first, and
      (ii) the respective direction in which each fluid of said pair is passed through said column being selected so that each fluid of said pair first contacts the stationary phase for which said peptide has lesser adsorption affinity and greater migration tendency in the presence of that fluid.

2. A method in accordance with claim 1 in which step (b) comprises at least two pairs of said fluids being passed through said column in opposite directions.

3. A method in accordance with claim 1 in which said first and second stationary phases are ion exchange resins differing according to electrostatic charge.

4. A method in accordance with claim 1 in which said first and second stationary phases differ according to hydrophobicity.

5. A method in accordance with claim 1 in which said first and second stationary phases are particulate solids.

6. A method for the removal and separation of a terminal amino acid from a peptide, in which said peptide is contacted with a series of reactants in accordance with a preselected protocol, said method comprising:
   (a) adsorbing said peptide on an adsorption column containing first and second stationary phases arranged in series therein and meeting at a common interface, said first and second stationary phases differing in adsorption characteristics and selected such that said peptide has affinity for at least one of said stationary phases;
   (b) reacting said peptide with said reactants in accordance with said preselected protocol by passing liquid solutions of said reactants in sequence through said column such that said peptide remains adsorbed on said column preferentially with respect to said reactants and said terminal amino acid which is thereby separated; and
   (c) subsequent to the passage of at least one reactant of said reactants, passing a wash liquid through said column in a direction opposite to that of said reactant, said wash liquid selected such that said peptide is partitioned between said wash liquid and said stationary phases in such a manner that said peptide has a lesser adsorption affinity for, and thereby a greater tendency for migration in, one of said stationary phases than the other, the directions of flow of said reactant and said wash liquid being selected such that said wash liquid first contacts the stationary phase for which said peptide has lesser adsorption affinity and greater migration tendency, thereby causing preferential migration of said peptide toward said interface.

7. A method in accordance with claim 6 in which the flows of at least two of said reactants through said column are each followed by flows in the opposite direction of respective wash liquids, in accordance with step (c).

8. A method in accordance with claim 6 in which said first and second stationary phases are ion exchange resins differing according to electrostatic charge.

9. A method in accordance with claim 6 in which said first and second stationary phases differ according to hydrophobicity.

10. A method in accordance with claim 6 in which said wash liquid is substantially non-polar and said reactants are contained in a polar medium.

11. A method in accordance with claim 6 in which said first stationary phase is hydrophilic and said second stationary phase is hydrophobic, and in which said wash liquid contains an organic solvent causing greater migration of said peptide through said second stationary phase than said first and causing said peptide to pass through said column in the direction from said second stationary phase to said first.

12. A method in accordance with claim 11 in which said organic solvent is a member selected from the group consisting of heptane, benzene, toluene, ethyl acetate, n-butyl acetate, and acetonitrile.

13. A method in accordance with claim 6 in which said first and second stationary phases are particulate solids.

14. A method in accordance with claim 6 in which said adsorption column is arranged vertically, step (b) comprises passing said reactants upward through said column, and step (c) comprises passing said wash liquid downward through said column.

15. A method in accordance with claim 6 in which step (b) includes the substeps:
   (i) coupling said terminal amino acid with a coupling agent, and
   (ii) reacting said peptide with a cleaving agent to cleave therefrom said terminal amino acid and coupling agent thus coupled;
said substeps performed by passing liquid solutions of said coupling and cleaving agents through said column in a given direction, each said substep being followed by passing a wash liquid in the opposite direction, said wash liquid being selected to provide said peptide with a lesser adsorption affinity for, and thereby a greater tendency for migration in, one of said stationary phases than the other, the directions of flow of said coupling and cleaving agents and said wash liquid being selected such that said wash liquid first contacts the stationary phase for which said peptide has lesser adsorption affinity and greater migration tendency, thereby causing preferential migration of said peptide toward said interface.

16. A method in accordance with claim 15 in which substeps (i) and (ii) are both performed in aqueous media, and said wash liquid flowed through said column following each said substep contains organic solvents which are at most only partially water-miscible.

17. A method in accordance with claim 15 in which:
said first stationary phase is hydrophilic and said second stationary phase is hydrophobic,
substeps (i) and (ii) are both performed in aqueous media flowing in a direction whereby said media contact said first stationary phase first and flow toward said second stationary phase,
said wash liquid passes through said column following each said substep, said wash liquid containing a hydrophobic organic solvent, and
said wash liquid is passed through said column in a direction whereby said wash liquid contacts said second stationary phase first and flows toward said first stationary phase.

18. A method in accordance with claim 17 in which said first stationary phase is a member selected from the group consisting of controlled pore glass and unsubstituted silica, and said second stationary phase is a member selected from the group consisting of ($C_4$-$C_{18}$ alkyl)-substituted silicas and hydrophobic polymeric resins.

19. A method for sequentially modifying a linear polymer by exposure to a series of fluids, said method providing for localization of said polymer during said exposures, said method comprising the steps of:
(a) adsorbing said polymer on an adsorption column having a stationary phase, the adsorption characteristics of said stationary phase being nonuniformly distributed so that
when a fluid of a first group of said fluids is conveyed through said column in a forward direction, the mobility of said polymer decreases along said column in said forward direction, and
when a fluid of a second group of said fluids is conveyed through said column in a reverse direction opposed to said forward direction, the mobility of said polymer decreases along said column in said reverse direction;
(b) conveying a fluid of said first group through said column in said forward direction so that said polymer migrates in said forward direction within said column without exiting said column;
(c) conveying a fluid of said second group through said column in said reverse direction so that said polymer migrates in said reverse direction within said column without exiting said column; and
(d) iterating steps b and c.

* * * * *